United States Patent
Wirbeleit

(10) Patent No.: US 7,787,108 B2
(45) Date of Patent: Aug. 31, 2010

(54) INLINE STRESS EVALUATION IN MICROSTRUCTURE DEVICES

(75) Inventor: Frank Wirbeleit, Dresden (DE)

(73) Assignee: Globalfoundries Inc., Grand Cayman (KY)

( * ) Notice: Subject to any disclaimer, the term of this patent is extended or adjusted under 35 U.S.C. 154(b) by 405 days.

(21) Appl. No.: 11/856,799

(22) Filed: Sep. 18, 2007

(65) Prior Publication Data

US 2008/0158541 A1 Jul. 3, 2008

(30) Foreign Application Priority Data

Dec. 29, 2006 (DE) ............ 10 2006 062 036

(51) Int. Cl.
*G01B 11/16* (2006.01)
(52) U.S. Cl. ............................................. 356/32
(58) Field of Classification Search .............. None
See application file for complete search history.

(56) References Cited

U.S. PATENT DOCUMENTS

| 6,483,580 | B1 * | 11/2002 | Xu et al. ............ 356/300 |
| 6,747,338 | B1 * | 6/2004 | Nunan et al. ......... 257/640 |
| 6,885,467 | B2 * | 4/2005 | Du-Nour et al. ...... 356/630 |
| 7,274,440 | B1 * | 9/2007 | Janik et al. ......... 356/365 |
| 7,295,307 | B2 * | 11/2007 | Naka et al. ......... 356/301 |
| 7,332,360 | B2 * | 2/2008 | Smayling et al. ...... 438/14 |
| 7,589,322 | B2 * | 9/2009 | Nishikata et al. ..... 250/310 |
| 2006/0098861 | A1 * | 5/2006 | See et al. ........... 382/145 |

FOREIGN PATENT DOCUMENTS

DE 10146826 B4 11/2004
DE 102004026145 A1 5/2006

OTHER PUBLICATIONS

Translation of Official Communication from German Patent Office for German Patent Application No. 10 2006 062 036.4 dated Dec. 22, 2009.

* cited by examiner

*Primary Examiner*—Gregory J Toatley, Jr.
*Assistant Examiner*—Juan D Valentin
(74) *Attorney, Agent, or Firm*—Williams, Morgan & Amerson, P.C.

(57) ABSTRACT

By performing optical measurements and evaluating the optical response of an appropriately prepared measurement site, stress-related characteristics, such as intrinsic stress of dielectric layers, may be evaluated due to the dependency of the optical response on stress-induced modifications of the charge carrier mobility of a conductive layer provided below the dielectric layer probed by an optical signal. Consequently, inline measurement results may be obtained in a highly efficient manner, thereby providing the potential for monitoring complex stress engineering strategies during a manufacturing sequence for forming microstructure devices.

20 Claims, 4 Drawing Sheets

INLINE STRESS EVALUATION IN MICROSTRUCTURE DEVICES

BACKGROUND OF THE INVENTION

1. Field of the Invention

Generally, the present disclosure relates to the field of manufacturing microstructure devices, such as microelectronic components in the form of integrated circuits and the like, and, more particularly, to the formation of stressed material layers in microstructure devices in order to adjust specific device characteristics, such as local charge carrier mobilities in channel regions of a field effect transistor and the like.

2. Description of the Related Art

During the fabrication of microstructure devices, various material layers are typically formed above an appropriate substrate and these layers are locally treated to obtain specific characteristics as required for the function of the device under consideration. The treatment of material layers may include patterning, i.e., the selective removal or deposition of materials, the modification of the conductivity of, for instance, semiconductor materials and the like. Recently, stress and strain engineering techniques have been established in order to adjust device characteristics in a global and local manner. Stress may occur in nearly any type of microstructure device, due to a thermal mismatch of various material layers and the like, and may require a thorough design of the device and the process flow, since respective stress components and the respective strain induced thereby may have a significant influence on the performance and the integrity of devices. On the other hand, stress and strain intentionally used in microstructure devices may significantly improve device characteristics in terms of performance, as will be exemplarily explained with respect to advanced silicon-based transistor elements, which represent a dominant circuit component of sophisticated integrated circuits.

Generally, a plurality of process technologies are currently practiced, wherein, for complex circuitry, such as microprocessors, storage chips and the like, MOS technology is currently the most promising approach, due to the superior characteristics in view of operating speed and/or power consumption and/or cost efficiency. During the fabrication of complex integrated circuits using MOS technology, millions of transistors, i.e., N-channel transistors and/or P-channel transistors, are formed on a substrate including a crystalline semiconductor layer. A MOS transistor, irrespective of whether an N-channel transistor or a P-channel transistor is considered, comprises so-called PN junctions that are formed by an interface of highly doped drain and source regions with an appropriately doped channel region disposed between the drain region and the source region. The conductivity of the channel region, i.e., the drive current capability of the conductive channel, is controlled by a gate electrode formed above the channel region and separated therefrom by a thin insulating layer. The conductivity of the channel region, upon formation of a conductive channel due to the application of an appropriate control voltage to the gate electrode, depends, among other things, on the dopant concentration, the mobility of the charge carriers, and, for a given extension of the channel region in the transistor width direction, on the distance between the source and drain regions, which is also referred to as channel length. Hence, in combination with the capability of rapidly creating a conductive channel below the insulating layer upon application of the control voltage to the gate electrode, the conductivity of the channel region substantially influences the performance of MOS transistors. Thus, the reduction of the channel length, and associated therewith the reduction of the channel resistivity, is a dominant design criterion for accomplishing an increase in the operating speed of the integrated circuits.

The continuing shrinkage of the transistor dimensions, however, entails a plurality of issues associated therewith that have to be addressed so as to not unduly offset the advantages obtained by steadily decreasing the channel length of MOS transistors, such as the adaptation and possibly the new development of highly complex process techniques required for patterning extremely scaled device features. Furthermore, some of the measures that are necessary for countering detrimental effects, such as short channel effects, i.e., a reduced controllability of the conductive channel, may have a negative impact on the charge carrier mobility in the channel region. Therefore, it has been proposed to also enhance device performance of the transistor elements by increasing the charge carrier mobility in the channel region by modifying the lattice structure in the channel region, for instance by creating tensile or compressive stress so as to produce a corresponding strain in the channel region, which results in a modified mobility for electrons and holes, respectively. Thus, the introduction of stress or strain engineering into integrated circuit fabrication is an extremely promising approach for further device generations, since, for example, strained silicon may be considered as a "new" type of semiconductor material, which may enable the fabrication of fast powerful semiconductor devices without requiring expensive semiconductor materials and manufacturing techniques.

Consequently, it has been proposed to introduce, for instance, global strain by means of a silicon/germanium layer or a silicon/carbon layer formed on a silicon substrate to obtain the desired strain in the channel region.

In other approaches, locally created stress produced by, for instance, overlaying layers, spacer elements, trench isolation structures and the like is used to create a desired strain within the channel region. However, the process of creating the strain in the channel region by applying a specified external stress may strongly depend on the device architecture, process techniques, materials used and the like, since the translation of the locally created stress into strain in the channel region is affected by, for instance, how strongly the channel region is bonded to the buried insulating layer in silicon-on-insulator (SOI) devices or the remaining bulk silicon in bulk devices, how much stress may be created during the formation of respective stressed layers and the like.

As a consequence, in advanced microstructure devices, such as integrated circuits, that are fabricated by using one or more of the above-identified techniques, the device characteristics may significantly depend on the stress levels provided in respective material layers, thereby requiring efficient techniques for monitoring the various stress sources of complex devices. However, the determination of internal stress levels of product substrates in a fast and accurate manner is extremely difficult and, hence, the bending of non-patterned test substrates having formed thereon a stressed material of interest is typically measured. In other cases, destructive Raman and micro-Raman techniques may be used to assess the stress conditions of patterned substrates at various process stages. While the measurement of dedicated non-patterned test substrates may not adequately represent the stress conditions on actual product substrates, the latter test procedures may be time-consuming, thereby providing the measurement results in a highly delayed manner.

The present disclosure is directed to various methods and systems that may avoid, or at least reduce, the effects of one or more of the problems identified above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the present disclosure relates to a technique for estimating stress characteristics in microstructure devices on the basis of optical measurement techniques, thereby providing the potential for monitoring and controlling stress and strain engineering strategies during the manufacturing process on the basis of optical measurement data obtained without a significant delay. Furthermore, the optical measurement technique for evaluating stress characteristics of microstructure devices during various manufacturing stages may be readily implemented into the manufacturing sequence substantially without unduly adding to process complexity. In some aspects, well-established optical measurement techniques may be used in combination with appropriate evaluation regimes. According to the principles of the subject matter disclosed herein, the influence of stress on the conductivity of a respective material, and in particular aspects on the charge carrier mobility in semiconductor materials, as previously explained, may be exploited in order to extract appropriate information contained in the optical response that depends on the electronic configuration of the respective conductive material. For instance, without intending to restrict the present disclosure to the following explanation, it is assumed that the interaction of electrons in the conduction band of the conductive material with an incoming radiation may depend on the mobility of the electrons, which in turn may significantly depend on a respective strain induced by, for instance, an overlying material, thereby providing a relative measure for the inherent stress of the strain-inducing mechanism, such as the overlying material layer. Since corresponding optical measurements may be readily performed on respective product substrates, for instance on the basis of respective measurement sites on the substrates, the corresponding stress-related characteristics of materials may be efficiently evaluated throughout the entire manufacturing sequence, for instance by appropriately preparing the respective measurement sites, that is, providing an appropriate conductive material, such as a semiconductor material, prior to receiving the material of interest, of which respective stress-related characteristics have to be evaluated. In other cases, appropriately designed test structures or even product features may be subjected to optical measurements in order to evaluate the stress characteristics of respective materials provided at specific manufacturing stages.

According to one illustrative embodiment, a method comprises optically probing a first material layer formed above a conductive second material layer, wherein the first and second material layers are formed above a portion of a substrate configured to form microstructure devices thereon. The method further comprises evaluating a stress characteristic of at least one of the first and second material layers on the basis of an optical response induced by the optical probing of the first material layer.

According to another illustrative embodiment, a method comprises forming a material layer above a substrate that comprises a device region for microstructure devices and a measurement region. Furthermore, an optical response induced by an optical beam that is directed to the measurement region is detected and a stress level of the material layer is evaluated on the basis of the optical response.

According to yet another illustrative embodiment, a metrology system for evaluating stress characteristics of microstructure devices comprises an optical radiation source configured to provide an optical probing beam to a restricted area of a substrate. The system further comprises an optical detector configured to receive an optical response to the optical probing beam. Finally, the system comprises an evaluation unit operatively connected to the optical detector and configured to determine a difference of the optical response with respect to a reference data corresponding to a predefined stress characteristic of the restricted area.

BRIEF DESCRIPTION OF THE DRAWINGS

The disclosure may be understood by reference to the following description taken in conjunction with the accompanying drawings, in which like reference numerals identify like elements, and in which.

Figure 1A:
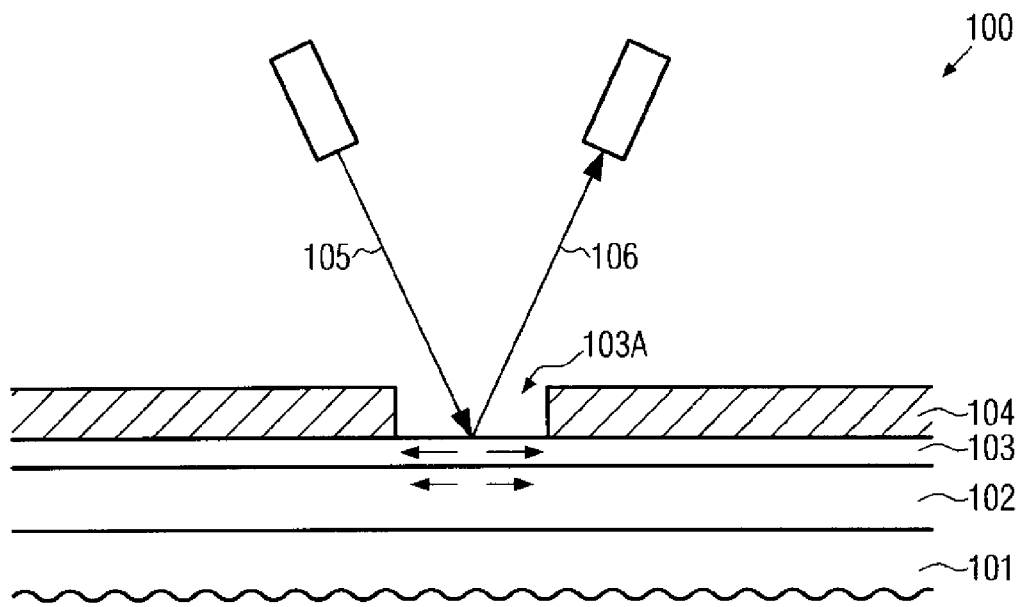
FIGS. 1a-1b schematically illustrate cross-sectional views of microstructure devices during an optical measurement procedure for probing material layers of different stress characteristics according to illustrative embodiments disclosed herein.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Generally, the present disclosure relates to a technique for enhancing stress and strain engineering concepts by evaluating stress-related characteristics, such as intrinsic stress levels of material layers and the like, on the basis of optical measurement techniques, such as ellipsometry, scatterometry and the like, in order to appropriately extract information on stress characteristics, which may be "encoded" into the respective optical response by the effect of a corresponding stress on the electron mobility of a conductive material formed below a respective material layer exposed to a probing optical beam. Thus, in some aspects, the intrinsic stress characteristics of material layers, which may typically be used for locally generating a desired degree of strain, such as in channel regions of advanced field effect transistors, may be efficiently evaluated, for instance with respect to complying with specified process margins, thereby efficiently contributing to enhanced process and device uniformity. In other aspects, the stress characteristics in semiconductor materials may be assessed at any appropriate manufacturing stage by providing an appropriate "probing" or "measurement" layer of dielectric material, which may represent any sacrificial or permanent material that may be used during the optical measurement procedure for evaluating the stress and strain characteristics of the underlying semiconductive material. For example, the strain characteristics in the semiconductive material may have a significant influence on the electron mobility, which may generally "shift" or vary the response to an incoming optical beam, for instance with respect to a different degree of reflectivity, depending on the stress level, wherein this shift or variation may be encoded into the optical response of a system including a dielectric layer of predefined characteristics in combination with the semiconductive material. Thus, for otherwise substantially identical conditions of the layer system, a difference of optical responses obtained for different stress levels may therefore be efficiently used in determining a meaningful statement on the correlation between the two different stress levels. Consequently, a nondestructive and fast measurement technique may be provided, which may enable efficient monitoring and evaluation of stress and strain engineering techniques at appropriate manufacturing stages, wherein, in some illustrative aspects, well-established optical measurement procedures, such as ellipsometry and/or scatterometry, may be used. Thus, the subject matter disclosed herein may be efficiently implemented in respective manufacturing environments and manufacturing sequences without significantly contributing to complexity in terms of metrology resources and the like.

FIG. 1a schematically illustrates a microstructure device 100 during a specific manufacturing stage. The microstructure device 100 may comprise a substrate 101, which may represent any appropriate carrier material for forming therein or thereon respective components, such as circuit elements for integrated circuits, micromechanical devices and the like. For instance, the substrate 101 may represent a silicon substrate, as, for instance, the vast majority of complex integrated circuits are, and will be in the foreseeable future, manufactured on the basis of silicon. The substrate 101 may, however, be provided in any other appropriate form, for instance as an insulating material, for example in the form of a glass substrate and the like. The substrate 101 may have formed thereon a layer of conductive material 102, which may be provided in the form of an appropriate semiconductor material, such as a silicon-based material, a silicon/germanium material or any other II-VI or III-V semiconductor compound. Furthermore, the substrate 101, in combination with the layer 102, may represent a silicon-on-insulator (SOI) configuration wherein the substrate 101 may be comprised of an insulating material or may at least comprise a buried insulating layer (not shown), such as silicon dioxide and the like. Furthermore, a dielectric material layer 103 may be formed on the conductive layer 102, wherein, in the illustrative embodiment shown, the dielectric material 103 may be provided as a material exhibiting a certain degree of intrinsic stress with respect to the layer 102. As previously explained, dielectric materials, such as silicon nitride, silicon dioxide and the like, may frequently be provided with a high intrinsic stress when formed on an underlying material layer, thereby also imparting a certain degree of stress to the underlying material. In sophisticated manufacturing techniques, a corresponding stress and strain inducing mechanism may be efficiently used so as to significantly modify the charge carrier mobility and thus the conductivity of semiconductor materials, as is previously explained. Thus, a respective intrinsic stress of the dielectric layer 103 may be intentionally provided so as to modify the electrical behavior of the conductive layer 102. For example, as indicated in FIG. 1a, the dielectric layer 103 may be formed on the layer 102 so as to have the tendency to expand, which may also result in a corresponding strain in the layer 102, thereby slightly modifying the lattice structure when the material of the layer 102 is provided in a substantially crystalline or polycrystalline configuration.

Furthermore, in the illustrative embodiment, a further material layer 104 may be provided, which may be patterned so as to expose a portion of the layer 103, thereby defining a measurement site 103A for performing an optical measurement process. It should be appreciated that the material layer 104 may not be necessary for defining the measurement site 103A and may not be present during the optical measurement process. In other cases, the layer 104 may represent other structural components of the device 100 that may be formed in respective device areas of the device 100. In other cases, the microstructure device 100 may represent the substrate 101 having formed thereon the layers 102 and 103, which may substantially entirely cover the substrate 101. Thus, the subject matter disclosed herein should not be considered as being restricted to a specific configuration of the microstructure device 100 as long as, at least locally, the layers 102 and 103 are provided and accessible for an optical measurement process in order to estimate stress-related characteristics of at least one of the layers 102 and 103.

The microstructure device 100 as shown in FIG. 1a may be formed on the basis of well-established process techniques, which may involve lithography, deposition, implantation, etch, anneal techniques and the like, according to device and process requirements. For instance, the dielectric layer 103 may be formed on the basis of well-established process techniques for providing a certain amount of intrinsic stress, wherein typically a high compressive or tensile stress may be formed in advanced semiconductor devices in order to enhance electron or hole mobility, respectively. For this purpose, well-established deposition techniques, such as chemical vapor deposition (CVD) may be used, in which process parameters, such as pressure, temperature, flow rates and in particular ion bombardment during the deposition process, may be adjusted in order to obtain a desired type and magnitude of intrinsic stress. However, respective process variations regarding one or more of these parameters may occur, thereby resulting in respective variations of the corresponding intrinsic stress. For this reason, the device 100 may be subjected to an optical measurement process using a probing optical beam 105 directed at the measurement site 103A in order to probe the layer 103, wherein optical characteristics of the material layer 103 may have a significant influence on the characteristics of a reflected beam 106 including the optical response to the probing beam 105. However, the optical characteristics of the material layer 103 may not necessarily significantly depend on the intrinsic stress of the layer 103 and may therefore require an additional stress-dependent "modulation." Thus, by providing the layer 102 having a moderately high sensitivity to a variation of electron mobility caused by the intrinsic stress of the layer 103, however, the optical response 106, which is also dependent on the interaction of the incident beam 105 with the surface of the layer 102 and thus with the corresponding free charge carriers contained therein, may therefore also be affected by the intrinsic stress of the layer 103. Consequently, by appropriately evaluating the optical response 106, a meaningful statement with respect to the intrinsic stress in the layer 103, at least in relation to reference data, may be obtained.

Figure 1B:
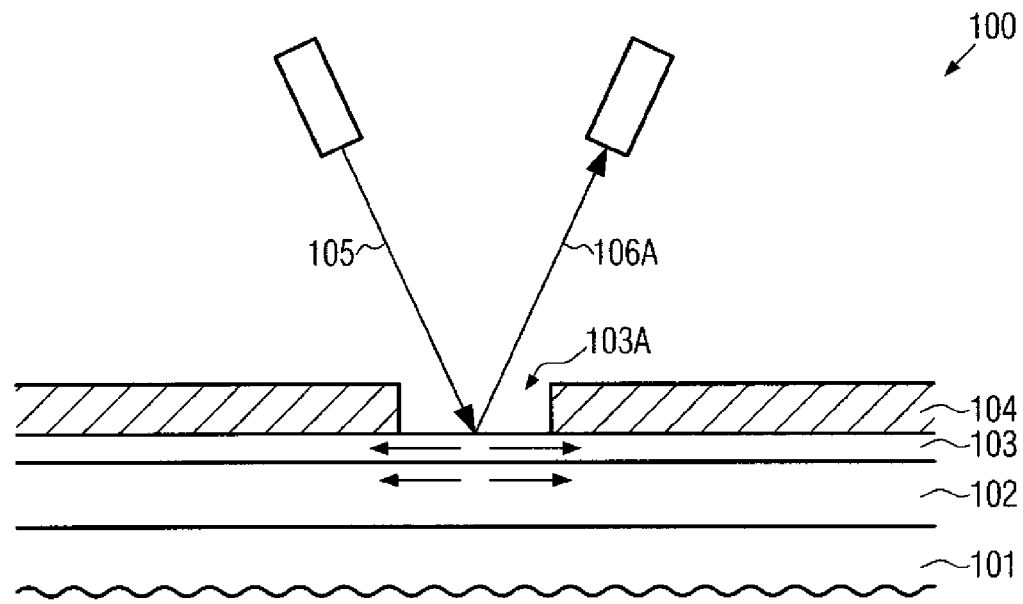

FIG. 1b schematically illustrates a microstructure device 100 or an equivalent microstructure wherein, for example, the stressed layer 103 may have been formed with a different intrinsic stress, due to process variations or other reasons, which may therefore result in a different induced degree of strain and thus influence on the corresponding charge carrier mobility in the layer 102. For example, the microstructure 100 as shown in FIG. 1b may represent a different portion of the substrate 101, wherein a local variation of process parameters may have caused a different amount of intrinsic stress compared to the device as shown in FIG. 1a. In other cases, the device in FIG. 1b may represent a configuration that is substantially identical to the device 100 in FIG. 1a, wherein, however, the layer 103 may have been formed on the basis of differently selected deposition parameters in order to obtain a different amount of intrinsic stress for otherwise substantially identical layer parameters, such as layer thickness, material composition and the like. Also, in this case, the device 100 may be subjected to an optical measurement process on the basis of identical process parameters as are used in FIG. 1a. Hence, the probing beam 105 is used and a corresponding optical response 106A may be detected, wherein the optical response 106A may differ from the response 106 due to the difference in charge carrier mobility in the region 102, as previously explained.

Figure 1C:
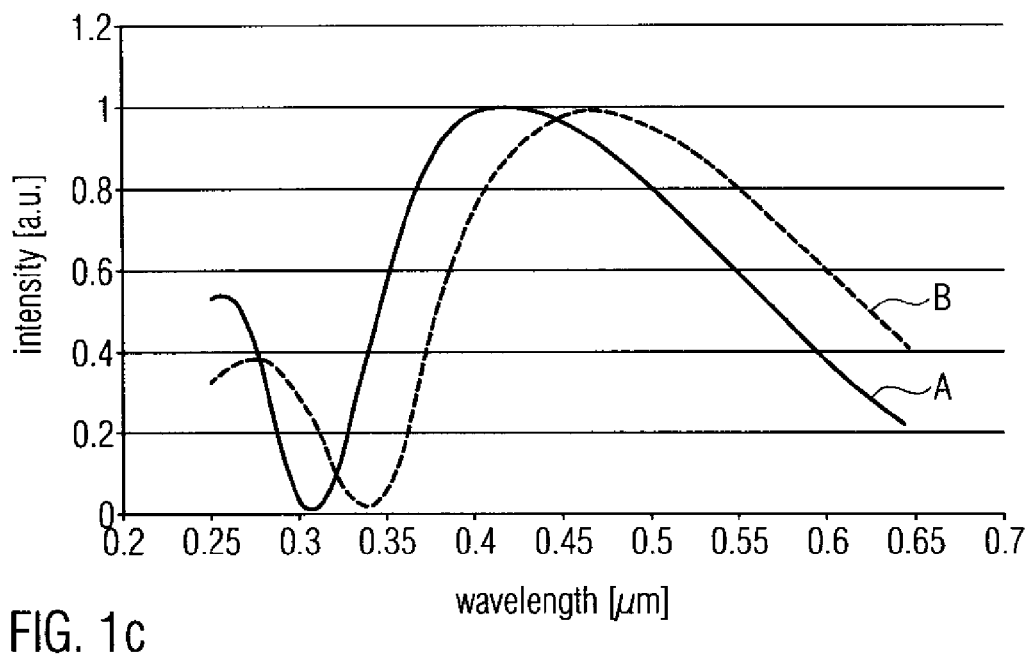
FIG. 1c schematically illustrates a difference in the optical response on the basis of respective spectra obtained by ellipsometry according to further illustrative embodiments disclosed herein.

FIG. 1c schematically illustrates a graph for illustrating appropriate representations of the optical responses 106, 106A. For instance, the probing beam 105 may be provided in the form of an optical signal including a specified wavelength range, which may also include a specific preparation, such as polarizing the corresponding beam 105 and the like. For instance, well-established ellipsometry techniques may be used, for instance based on spectroscopic ellipsometry, in order to provide the probing beam 105. Based on appropriate detection techniques, which may also involve analysis procedures including polarization and the like, the wavelength-dependent intensity of the optical responses 106, 106A may be obtained, which may be shown in the form of respective spectra represented by curves A and B. For instance, curve B may correspond to the optical response 106, wherein it may be assumed that the corresponding intrinsic stress of the layer 103 may result in a reduced electron mobility compared to the situation as shown in FIG. 1b, from which the optical response 106A may be obtained. Consequently, the spectrum B, that is pronounced maxima and minima thereof, corresponding to the response 106 may be shifted towards increased wavelength values compared to the spectrum A corresponding to the optical response 106A. Consequently, the corresponding difference of the optical responses 106 and 106A, which may be determined on the basis of the spectra A and B, may represent a corresponding difference in the respective intrinsic stresses of the layers 103 of the devices 100 in FIGS. 1a and 1b.

For example, representative points of the spectra A and B may be determined and may be used for obtaining a corresponding difference, wherein the respective difference may be normalized or weighted with respect to one of the spectra A and B, when one of these spectra is to be considered as a reference spectrum. For example, during a corresponding manufacturing sequence, in which a plurality of substrates may be processed so as to obtain the dielectric layer 103, one of the corresponding substrates may be used as a reference substrate so as to monitor the process uniformity of the corresponding deposition process for forming the layers 103 on a plurality of substrates. It should be appreciated that, typically, respective process non-uniformities with respect to a variation of layer thickness may be less critical compared to a precise adjustment of the stress level of the layer 103 so that corresponding differences in the respective optical responses may be substantially determined by the intrinsic stress levels rather than by other layer properties. In other cases, the corresponding layer characteristics, such as thickness, material composition and the like, may be determined on the basis of other measurements, which may also involve optical measurement processes, wherein, however, an influence of the intrinsic stress in the layer 103 may be significantly reduced to enable a determination of the respective layer characteristic without significant interference by the amount of intrinsic stress in the layer 103. For instance, in dedicated measurement sites, a further material layer may be provided between the layers 102 and 103 which may substantially decouple the respective optical response from the characteristics of the layer 102. Furthermore, the size of the corresponding measurement site may be selected such that the corresponding deposition behavior for forming the layer 103 may be substantially identical in the measurement site 103A and other measurement sites for determining other layer characteristics, such as thickness, index of refraction and the like.

In some illustrative embodiments, the optical responses 106A, 106 may also be analyzed with respect to a difference in layer thickness, wherein it may be assumed that a difference in the distance between maximum and minimum values of the respective spectra A, B may substantially originate from the respective differences in a thickness of the respective layers 103, while a corresponding shift of the respective maximum and minimum values may be caused by the difference in electron mobility and thus intrinsic stress of the layers 103.

It should be appreciated that the optical responses 106, 106A may be subjected to any appropriate data manipulation process to obtain appropriate data, which may be compared with each other in order to identify a deviation of the intrinsic stress of the layers 103. For example, appropriate filtering techniques, data fit processes and the like may be used to obtain appropriate data, such as spectra A, B. However, the spectra A, B may be subjected to a further data manipulation, for instance for determining extreme values, slopes, integrals and the like, as may be appropriate for evaluating the stress characteristics of the layers 103. In some illustrative embodiments, a Fourier transformation may be performed on the basis of the spectra A, B in order to extract appropriate Fourier components enabling an efficient comparison of the corresponding optical responses 106, 106A.

Figure 1D:
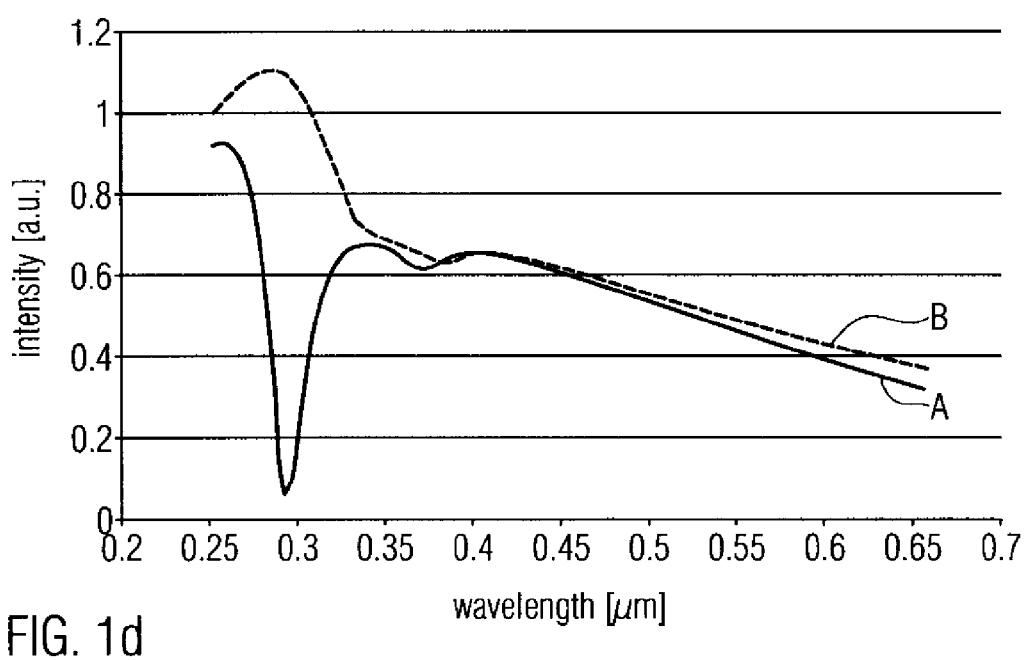
FIG. 1d schematically illustrates a graph including a spectrum obtained by manipulating measurement data on the basis of a Fourier transformation in order to identify a difference in stress levels of respective material layers according to further illustrative embodiments disclosed herein.

FIG. 1d schematically illustrates a representation of corresponding cosine terms of the fourth order component of respective Fourier transformations for the curves A, B. As is evident from FIG. 1d, a significant difference of the respective Fourier components corresponding to curves B and A may occur, thereby efficiently enabling quantitatively determining a difference between the responses 106 and 106A. Consequently, stress characteristics of the microstructure device 100 corresponding to a specific manufacturing stage, which may require the deposition of the stressed layer 103, may be efficiently monitored, wherein appropriate reference data may be provided, for instance in the form of respective measurement data, so as to evaluate the corresponding microstructure devices 100 on the basis of the reference data. It should be appreciated that when the layer 103 has to be provided in a manufacturing stage in which the layer 103 may not be directly formed on the conductive layer 102 in device areas other than the measurement site 103A, appropriate patterning processes may be performed so as to expose the layer 102 in the measurement site 103A, for instance based on a corresponding mask, such as the layer 104, while maintaining any intermediate materials formed above the conductive layer 102 in device areas other than the measurement site 103A at this specific manufacturing stage. Thereafter, the layer 103 may be deposited in accordance with process requirements, wherein the layer 103 may be directly formed on the layer 102 in the measurement site 103A, thereby providing a device configuration as shown in FIGS. 1a and 1b. In other illustrative embodiments, the layer 102 may be locally provided in the measurement site 103A, for instance by depositing the layer 102 and selectively removing the layer 102 outside the measurement site 103A, and thereafter the dielectric layer 103 may be deposited based on device requirements. Thus, the optical measurement technique may provide a high degree of flexibility in monitoring the stress characteristics of dielectric layers to be formed at any appropriate manufacturing stage.

It should be appreciated that a stress in the conductive layer 102 may not necessarily be created by an overlying layer, such as the layer 103, but may have been established by other mechanisms, such as epitaxially grown semiconductor materials having a slight lattice mismatch to other semiconductor areas so as to create a respective strain in the layer 102. Also, in this case, the optical measurement technique described above may be efficiently used, thereby forming the layer 103 as a substantially stress-free layer in order to not unduly affect the overall stress or strain existing in the conductive layer 102 by the stress characteristics of the layer 103. Thus, the respective substantially stress-free layer 103 may then be used as a "measurement" layer in order to obtain the respective optical responses 106, 106A, affected by the respective electron mobilities, which are determined by the corresponding intrinsic strain in the conductive layer 102. In this case, depending on device requirements, the layer 103 may represent a sacrificial layer which may be removed after the optical measurement process, or may be a permanent layer if it is compatible with the further processing and the device requirements.

Figure 1E:
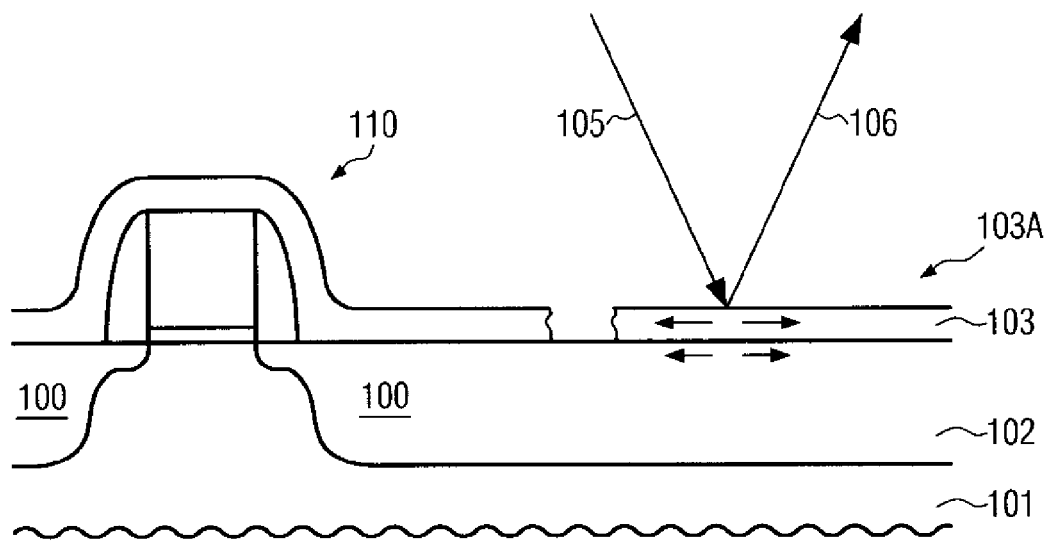
FIGS. 1e-1f schematically illustrate a cross-sectional view of microstructure devices during an optical measurement procedure for estimating stress characteristics for a substantially non-patterned measurement site (FIG. 1e) and a patterned measurement site (FIG. 1f) according to illustrative embodiments disclosed herein.

FIG. 1e schematically illustrates a cross-sectional view of the microstructure device 100 according to a further illustrative embodiment, wherein a device region 110 may comprise a transistor element having formed thereon the stressed layer 103, which may comprise, for instance, silicon nitride so as to induce a desired type of strain within the transistor element within the region 110. The layer 103 is also formed in the measurement site 103A, wherein the conductive layer 102 may have substantially the same dopant concentration compared to respective drain and source regions 111, while, in other embodiments, the dopant concentration in the layer 102 may significantly differ from that of the transistor in the region 110. In some illustrative embodiments, the layer 102 in the measurement site 103A may have a substantially non-doped configuration so as to reduce the effect of non-uniformities of respective ion implantation processes on the optical response 106 in order to provide increased sensitivity to variations of intrinsic stress of the layer 103. Thus, after forming the layer 103, a corresponding measurement process may be performed as previously described, wherein one or more optical responses 106 obtained from different measurement sites 103A of the same device or from different devices may be compared relative to each other. Consequently, a corresponding strain-inducing mechanism provided, for instance, on the basis of stressed layers enclosing respective transistor elements, such as the dielectric layer 103 as shown in FIG. 1e, may be efficiently monitored with respect to process variations, thereby contributing to enhanced process and thus device performance uniformity. Consequently, complex strain engineering techniques using stressed overlayers, strained or relaxed semiconductor materials and the like may be efficiently monitored and evaluated, wherein a substrate internal spatial resolution may be determined by the number and location of respective measurements sites 103A.

Figure 1F:
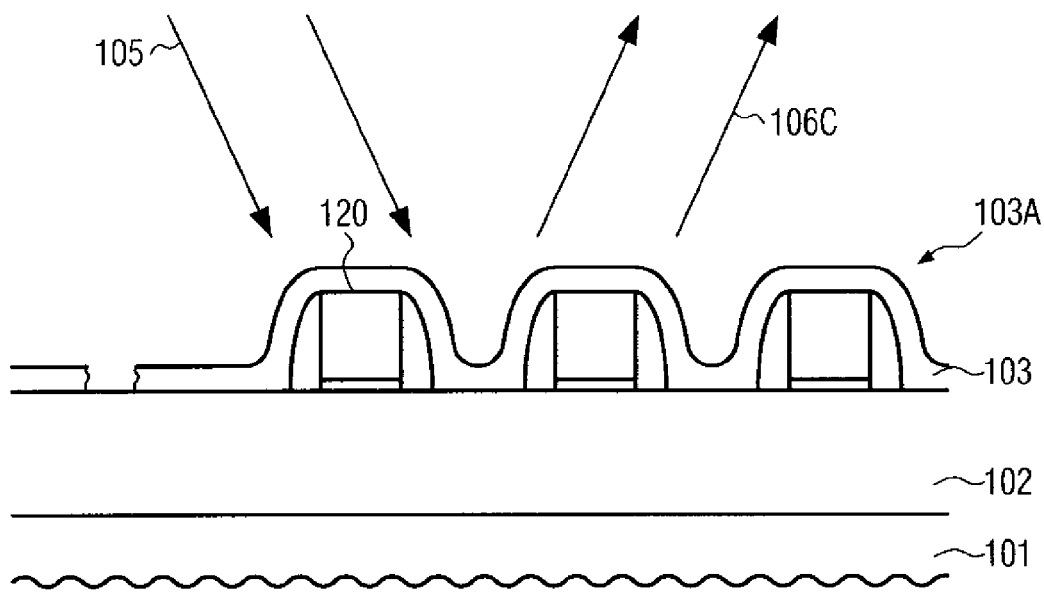

FIG. 1f schematically illustrates the microstructure device 100 according to yet another illustrative embodiment, in which the measurement site 103A may comprise a pronounced surface topography, which may be obtained on the basis of respective device features 120 which, in some illustrative embodiments, may have similar dimensions compared to actual device features, such as transistor elements as shown in FIG. 1e. Also, in this case, the dielectric layer 103 may be formed with intrinsic stress, wherein the efficiency of the corresponding stress-inducing mechanism may be evaluated on the basis of optical measurement techniques, as previously described. Hence, the probing incident beam 105 may be directed at the measurement site 103A, thereby generating a corresponding optical response 106C which may, however, compared to the responses 106, 106A, exhibit a significantly increased degree of complexity due to the pronounced surface topography. In some illustrative embodiments, the respective features 120 may provide a substantially periodic structure so that powerful data analysis techniques may be used, as are well-established in the field of scatterometry measurement techniques. That is, respective reference data may be used which may be maintained in respective libraries and the like in order to extract meaningful data with respect to stress-related characteristics defined by the layer 102 in combination with the layer 103. As previously explained with reference to FIG. 1e, also, in this case, in some embodiments, the features 120 may be formed while omitting specific manufacturing processes, such as implantation processes, in order to reduce the influence of these processes with respect to the evaluation of stress-induced characteristics. For example, the features 120 may be formed in accordance with design rules in order to estimate the effect of the stressed layer 103 in densely packed device areas, in which, for instance, the respective distances between neighboring gate electrodes may have a significant influence on the deposition behavior as well as the stress transfer characteristics.

For evaluating the optical responses 106 obtained from the patterned measurement site 103A, respective reference data may be used, which correspond to substantially identical structures except for the stress level induced by the layer 103 and/or by other mechanisms influencing the electron mobility at least on the layer 102. For instance, respective measurement sites may be provided in which the corresponding features 120 may be formed according to the same design principles as the features 120 in the site 103A, wherein, however, respective strain-inducing mechanisms may be omitted or may be included on the basis of well-controllable conditions. For example, the layer 103 may be locally formed on the basis of less critical stress determining process parameters, while otherwise providing substantially the same optical characteristics compared to the layer 103 having the high intrinsic stress. Hence, the difference in the optical responses may then be determined by the different stress conditions and may therefore represent a meaningful metric for evaluating the process under consideration. During the data evaluation, respective spectra may be obtained which may have, however, a significantly more complex structure compared to the spectra as shown in FIGS. 1c-1d. Due to appropriate reference data, which may, for instance be obtained in the above-described manner, or on the basis of other data manipulation schemes, as are used in scatterometry techniques, i.e., determining structural details of complex surface topography having a periodic structure on the basis of optical spectra, nevertheless, stress-dependent characteristics may be extracted.

Figure 2:
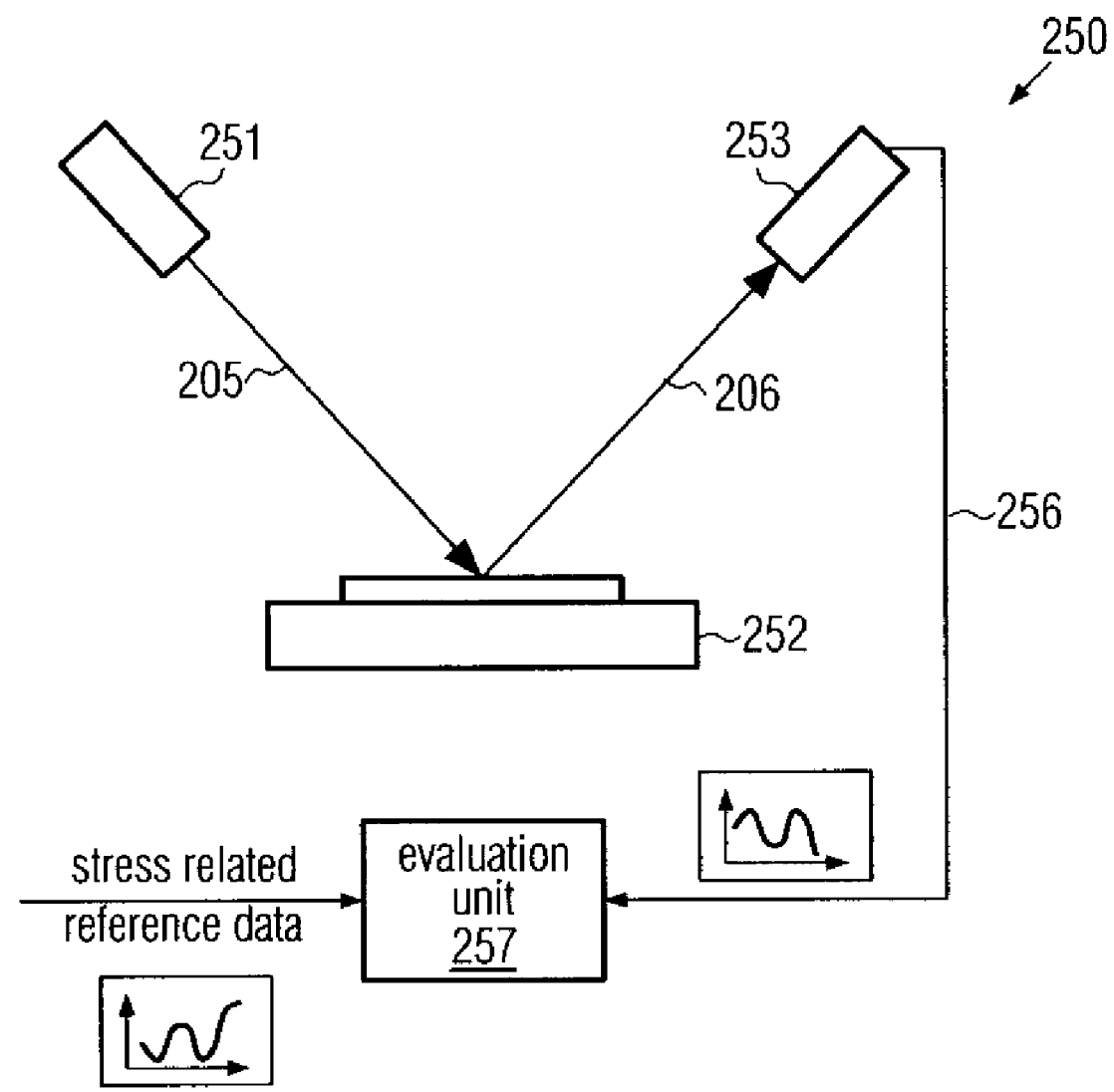
FIG. 2 schematically illustrates a metrology system based on optical measurement techniques and including an evaluation unit for estimating stress-related characteristics according to illustrative embodiments disclosed herein.

FIG. 2 schematically illustrates a metrology system 250 for performing optical measurements for evaluating stress characteristics of microstructure devices, as previously described. The metrology system 250 may include a light source 251 that is configured to emit a light beam 205 of predefined optical characteristics. The light source 251 may be any appropriate source of radiation that may be used in providing the light beam 205 such that respective layers or measurement sites of interest may be appropriately illuminated. To this end, the light source 251 may include any optical system (not shown) to provide the radiation emitted by the light source 251 with required characteristics. For example, the light source 251 may be adapted to provide a linearly polarized light beam with varying wavelength in the range of approximately 200-1000 nm. The metrology system 250 may further comprise a detector 253 adapted and arranged to receive a light beam 206 scattered or reflected by a substrate, such as the microstructure devices 100 previously described, that is mounted on a substrate holder 252. The detector 253 may also be configured to provide an output signal 256 indicative of at least a portion of the optical characteristics of the received light beam 206, which may include the optical response of the measurement site illuminated by the incident beam 205. The light source 251 and the detector 253 may be connected to a control unit 257 that may be configured to receive the output signal 256 and respective stress-related reference data, which may be obtained on the basis of actual measurement data and the like, as is previously described. The control unit 257 may be configured to appropriately compare respective data conveyed by the data 256 with the corresponding reference data to evaluate stress-related characteristics of the optical response contained in the beam 206. For this purpose, respective data manipulation algorithms, as, for instance, described with reference to the optical responses 106, 106A, may be implemented in the unit 257. In some illustrative embodiments, the metrology system 250 may be configured to perform ellipsometry measurement processes on the basis of the light source 251, the detector 253 and the substrate holder 252, wherein the corresponding signal 256 may be estimated by the unit 257 on the basis of the previously described techniques to provide a highly efficient inline evaluation of stress-related characteristics. In other cases, well-established scatterometry techniques may be used, for instance on the basis of appropriately created reference data, wherein the unit 257 may have implemented therein the respective computational resources to extract a corresponding shift of data obtained from the signal 256 with respect to the corresponding reference data, wherein the corresponding shift may be caused by a corresponding stress-related influence on charge carrier mobility, as is previously described.

As a result, the subject matter disclosed herein provides a technique for measuring stress levels and variations of stresses in material layers during the manufacturing process, for instance in the form of inline measurements, thereby providing the potential for obtaining a thorough understanding and monitoring of process techniques and device performance with respect to stress-related characteristics. In some aspects, well-established measurement strategies, such as ellipsometry, scatterometry and the like, may be used wherein respective measurement sites in actual product substrates may enable a substantially direct and non-delayed measurement of respective stress-related device and process characteristics. To this end, the variation of the response of quasi-free electrons at an interface of a conductive material and a dielectric material to in incoming optical beam, inducing an oscillation of the electrons, also referred to as plasmons, may be used to detect a corresponding shift of spectra obtained for different stress levels. Thus, this plasmon shift during the interaction with the probing optical beam may give an accurate indication of the stress level in the conductive layer, in particular in a semiconductor layer, which may be highly sensitive to a variation of strain induced therein. When the induced strain is at least partially induced by an overlaying dielectric material, the stress levels of this layer may thus be efficiently evaluated. In other cases, appropriate measurement layers may be provided above respective conductive layers, such as semiconductor layers, in order to optically determine the corresponding strain level therein, irrespective of the strain-inducing mechanism involved.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:

optically probing a first material layer formed above a conductive second material layer, said first and second material layers formed above a portion of a substrate configured to form microstructure devices thereon, wherein a third material layer is formed over said first material layer and an opening is formed in said third material layer to define a measurement site exposing said first material layer; and evaluating a stress characteristic of at least one of said first material layer and said second material layer on the basis of an optical response induced by optically probing said first material layer.

2. The method of claim 1, wherein said second conductive layer comprises a semiconductor material.

3. The method of claim 1, wherein evaluating said stress characteristic comprises comparing said optical response with reference data.

4. The method of claim 1, wherein said optical response is used to generate a spectrum of a specified wavelength range, said spectrum comprising at least a portion of information contained in said optical response.

5. The method of claim 4, wherein evaluating said stress characteristic comprises determining a difference of said spectrum with respect to a reference spectrum.

6. The method of claim 4, wherein generating said spectrum comprises generating a first spectrum and performing a Fourier transformation to generate a second spectrum.

7. The method of claim 1, wherein at least said first material is formed above a device region of said substrate, said device region comprising one or more features of a microstructure device.

8. The method of claim 1, wherein optically probing said first material layer and obtaining said optical response comprises performing an ellipsometry process.

9. The method of claim 1, wherein optically probing said first material layer and obtaining said optical response comprises performing a scatterometry measurement process.

10. A method, comprising:
forming a material layer above a substrate, said substrate comprising a device region for microstructure devices and a measurement region, wherein a second material layer is formed over said material layer and an opening is formed in said second material layer to define a measurement site exposing said material layer;

detecting on optical response induced by an optical beam directed to said measurement site; and evaluating a stress level of said material layer on the basis of said optical response.

11. The method of claim 10, further comprising forming a conductive layer at least in said measurement region prior to forming said material layer.

12. The method of claim 10, wherein evaluating said stress level comprises comparing at least a portion of data representing said optical response with reference data corresponding to a reference stress level.

13. The method of claim 10, further comprising generating a spectrum of a predefined wavelength range from said optical response.

14. The method of claim 13, wherein generating said spectrum comprises generating a first spectrum and performing a Fourier transformation to generate said spectrum.

15. The method of claim 13, further comprising determining at least one characteristic value from said spectrum, said at least one characteristic value indicating a difference with respect to a reference value.

16. The method of claim 10, wherein detecting an optical response comprises performing an ellipsometry process.

17. The method of claim 10, wherein said material layer has a non-planar surface topography.

18. The method of claim 17, wherein detecting an optical response comprises performing a scatterometry measurement process.

19. A metrology system for evaluating stress characteristics of microstructure devices, comprising:
an optical radiation source configured to provide an optical probing beam to a restricted area of a substrate, wherein said restricted area comprises a first material layer and a second material layer formed over said first material layer, and an opening is formed in said second material layer to define a measurement site exposing said first material layer;

an optical detector configured to receive an optical response to said optical probing beam; and an evaluation unit operatively connected to said optical detector and configured to determine a difference of said optical response with respect to a reference data corresponding to a predefined stress characteristic of said restricted area.

20. The metrology system of claim 19, wherein said evaluation unit is configured to determine said difference on the basis of a spectrum generated from said optical response and a reference spectrum defined by said reference data.

* * * * *